(12) United States Patent
Hoyt

(10) Patent No.: US 8,322,219 B2
(45) Date of Patent: Dec. 4, 2012

(54) PSEUDORANDOM BINARY SEQUENCE APPARATUS AND METHOD FOR IN-LINE INSPECTION TOOL

(75) Inventor: Philip M. Hoyt, Murray, UT (US)

(73) Assignee: Pure Technologies Ltd., Calgary (CA)

( * ) Notice: Subject to any disclaimer, the term of this patent is extended or adjusted under 35 U.S.C. 154(b) by 232 days.

(21) Appl. No.: 12/538,104

(22) Filed: Aug. 7, 2009

(65) Prior Publication Data
US 2010/0288049 A1   Nov. 18, 2010

Related U.S. Application Data

(60) Provisional application No. 61/087,537, filed on Aug. 8, 2008.

(51) Int. Cl.
 *G01N 29/00* (2006.01)
 *G01N 27/82* (2006.01)
(52) U.S. Cl. .............................. 73/602; 73/643; 324/240
(58) Field of Classification Search ..................... 73/602, 73/52, 61.49, 61.75, 64.42, 64.53, 599, 643; 324/240

See application file for complete search history.

(56) References Cited

U.S. PATENT DOCUMENTS

| | | |
|---|---|---|
| 3,341,771 A | 9/1967 | Crouch et al. |
| 3,437,810 A | 4/1969 | Wood et al. |
| 3,940,689 A | 2/1976 | Johnson, Jr. |
| 4,045,796 A | 8/1977 | Kline, Jr. |
| 4,100,809 A | 7/1978 | Bobrov et al. |
| 4,127,035 A | 11/1978 | Vasile |
| 4,295,214 A | 10/1981 | Thompson |
| 4,471,658 A * | 9/1984 | Morimoto ..................... 73/643 |
| 4,691,572 A | 9/1987 | van den Berg et al. |
| 5,085,082 A | 2/1992 | Cantor et al. |
| 5,126,654 A | 6/1992 | Murphy et al. |
| 5,283,768 A | 2/1994 | Rorden |
| 5,406,530 A | 4/1995 | Yamamoto |
| 5,454,276 A | 10/1995 | Wernicke |
| 5,537,876 A | 7/1996 | Davidson et al. |
| 5,581,037 A | 12/1996 | Kwun et al. |
| 5,608,164 A * | 3/1997 | MacLauchlan ................ 73/599 |
| 5,684,406 A * | 11/1997 | MacLauchlan et al. ...... 324/700 |
| 5,793,205 A | 8/1998 | Griffith et al. |
| 6,065,348 A | 5/2000 | Burnett |
| 6,179,084 B1 | 1/2001 | Yamamoto et al. |

(Continued)

OTHER PUBLICATIONS

Beuker, Thomas et al., "SCC Detection Improvement Using High Resolution EMAT Technology," International Pipeline Pigging, Integrity Assessment and Repair Conference, Houston, TX, Feb. 5-6, 2004.

(Continued)

*Primary Examiner* — J M Saint Surin
(74) *Attorney, Agent, or Firm* — Warren M. Pate, LLC

(57) ABSTRACT

An in-line inspection tool is disclosed for inspecting the wall of a pipeline while traveling therethrough. The in-line inspection tool may include a transmitter, a signal generator, one or more receivers, and a decoder. The signal generator may generate a pseudorandom signal, generate an inspection signal, and drive the transmitter with a convolution of the pseudorandom signal and the inspection signal. The transmitter may transmit the convoluted signal to the wall of the pipeline. One or more receivers may receive from the wall of the pipeline a received signal comprising at least one of the convoluted signal and a reflection of the convoluted signal. The decoder may identify the inspection signal within the received signal by cross correlating the received signal and the pseudorandom signal.

20 Claims, 9 Drawing Sheets

U.S. PATENT DOCUMENTS

| | | | |
|---|---|---|---|
| 6,243,657 B1 | 6/2001 | Tuck et al. | |
| 6,295,677 B1 | 10/2001 | Kwun et al. | |
| 6,298,732 B1 | 10/2001 | Burnett | |
| 6,359,434 B1 | 3/2002 | Winslow et al. | |
| 6,404,189 B2 | 6/2002 | Kwun et al. | |
| 6,424,150 B2 | 7/2002 | Kwun et al. | |
| 6,597,997 B2 | 7/2003 | Tingley | |
| 6,647,804 B1 * | 11/2003 | Deines | 73/861.18 |
| 6,666,095 B2 | 12/2003 | Thomas et al. | |
| 6,766,694 B2 * | 7/2004 | Hubschen | 73/643 |
| 6,823,488 B1 * | 11/2004 | Heegard et al. | 714/786 |
| 7,042,223 B2 | 5/2006 | Cull | |
| 7,271,575 B2 | 9/2007 | Pickerd et al. | |
| 7,426,867 B2 | 9/2008 | Koch | |
| 7,577,260 B1 * | 8/2009 | Hooley et al. | 381/77 |
| 2001/0017541 A1 | 8/2001 | Kwun et al. | |
| 2004/0136438 A1 | 7/2004 | Fullerton et al. | |
| 2007/0017822 A1 | 1/2007 | Gill et al. | |
| 2008/0092672 A1 | 4/2008 | Gibson | |
| 2009/0078048 A1 | 3/2009 | Alers et al. | |

OTHER PUBLICATIONS

Shevaldykin, V.G. et al., "EMA Transformation in Pulsed Magnetic Field and its Use in Portable Instruments for Acoustic Measurements," 16th World Conference on NDT, Montreal, Canada, Aug. 30-Sep. 3, 2004.

Aron, Jeff et al., "Development of an EMAT In-Line Inspection System for Detection, Discrimination, and Grading of Stress Corrosion Cracking in Pipelines," U.S. Department of Energy Award No. DE-FC26-01NT41154, Feb. 2005.

Klann, Martin et al., "Pipeline Inspection with the High Resolution EMAT ILI-Tool: Report on Field Experience," Proceedings of IPC 2006 6th International Pipeline Conference, Calgary, Alberta, Canada, Sep. 25-29, 2006.

Wong, Joe, "Application of Pseudorandom m-Sequences for Seismic Acquisition," CSPG CSEG Convention, Calgary, Alberta, Canada, May 14-17, 2007.

Beuker, Thomas et al., "In-line Inspection with High Resolution EMAT Technology Crack Detection and Coating Disbondment," International Pipeline Pigging, Integrity Assessment and Repair Conference, Houston, TX, Feb. 12-13, 2008.

* cited by examiner

PSEUDORANDOM BINARY SEQUENCE APPARATUS AND METHOD FOR IN-LINE INSPECTION TOOL

RELATED APPLICATIONS

This application claims the benefit of U.S. Provisional Patent Application Ser. No. 61/087,537 filed Aug. 8, 2008, which is hereby incorporated by reference.

BACKGROUND

1. Field of the Invention

This invention relates to pipeline inspection tools, and more particularly to apparatus and methods for data collection and analysis for an in-line inspection tool.

2. Background of the Invention

Oil, petroleum products, natural gas, hazardous liquids, and the like are often transported using pipelines. The majority of these pipelines are constructed from steel pipe. Once installed, a pipeline will inevitably corrode or otherwise degrade. Proper pipeline management requires identification, monitoring, and repair of defects and vulnerabilities of the pipeline. For example, information collected about the condition of a pipeline may be used to determine safe operating pressures, facilitate repair, schedule replacement, and the like.

Typical defects of a pipeline may include corrosion, gouges, dents, and the like. Corrosion may cause pitting or general wall loss, thereby lowering the maximum operating pressure of the pipeline. Vulnerabilities may also include curvature and bending anomalies and combined stress and chemical or biological action such as stress corrosion cracking. Without detection and preemptive action, all such defects and vulnerabilities may lead to pipeline failure.

Information on the condition of a pipeline is often collected using an in-line inspection tool. Ferromagnetic pipelines can be inspected for defects including cracks along the axis of a pipe by a limited number of technologies. These technologies include magnetic flux leakage (MFL), ultrasonic inspection (UT), eddy current inspection, and, in certain limited applications, electromagnetic acoustic transducers (EMAT).

Many in-line inspection tools use a pulsed signal source and sensors to collect information about a pipeline as they travel therethrough. In the past, in-line inspection tools have used technologies such as ultrasonic transducer (UT) inspection, eddy current inspection, electromagnetic acoustic transducer (EMAT) inspection and other technologies involving a transmitted and received energy pulse. Such technologies have been limited by low relative signal strength and low signal to noise ratio, further compromised by the noisy background of the pipeline environment.

While some technologies are more adversely affected by these factors than other are, all such techniques can be improved with better signal detection and recognition. What is needed is a better device and method for the generation and reception of pulsed signals for the various inspection technologies.

SUMMARY

In-line inspection (ILI) tools for inspecting pipelines utilize technologies that generate signals with low signal strength and consequent low signal-to-noise ratios. These technologies may include, but are not limited to, ultrasonic inspection (UT), eddy current inspection (ECI), electromagnetic acoustic transducer (EMAT) inspection using both Lohrentz force and magnetostrictive technologies, and some forms of magnetic flux leakage (MFL) inspection.

The prevailing approach to producing an acceptable signal-to-noise ratio is to increase the strength of the incident signal and the sensitivity of the sensing device. Some systems use other techniques in addition, but existing in-line inspection tools produce workable devices by maximizing their signal-to-noise ratios. In many instances, this approach produces devices with marginal detection capability. Moreover, this approach certainly limits the applicability to pipeline inspection of technologies that are in use in other fields. In view of the foregoing, certain embodiments in accordance with the present invention provide an alternative to attempts at improving the signal-to-noise ratio as a means of detecting inspection signals.

In selected embodiments, systems in accordance with the present invention may combine or convolute pseudorandom binary sequences (PRBS) or pseudorandom noise into the transmitted inspection signal. By so doing, signals with low strength or signals that are obscured by the background noise become visible. Even when signal-to-noise ratios are low, even when they may be less than one, the signal received in response to an anomaly such as a crack or corrosion may still be detected and analyzed. Cross correlation of PRBS convoluted signals detected in noisy environments supports suppression of the background noise, producing a visible signal even when signal-to-noise ratios may be comparable to, or less than, background levels.

Additionally, for maximum effectiveness, special mounting may be required to position a sensing device in proximity to the pipe wall. Selected embodiments in accordance with the present invention may include a mounting system maintaining the inspection system in contact with the pipe wall as the in-line inspection tool travels inside the pipe being inspected.

Accordingly, selected embodiments in accordance with the present invention provide apparatus and methods for developing a PRBS signal, convoluting that signal with an incident inspection signal, transmitting the convoluted signal through the pipe wall where it may be affected by pipeline anomalies, detecting the affected convoluted signal, and cross correlating or decoding the signal to suppress background noise and produce a signal that may be used to characterize anomalies.

Certain embodiments of the present invention may be discussed or illustrated in the context of an in-line inspection tool using EMAT technologies. However, concepts in accordance with the present invention are not limited to EMAT technologies and may be applicable to other in-line inspection technologies.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION

Figure 1:
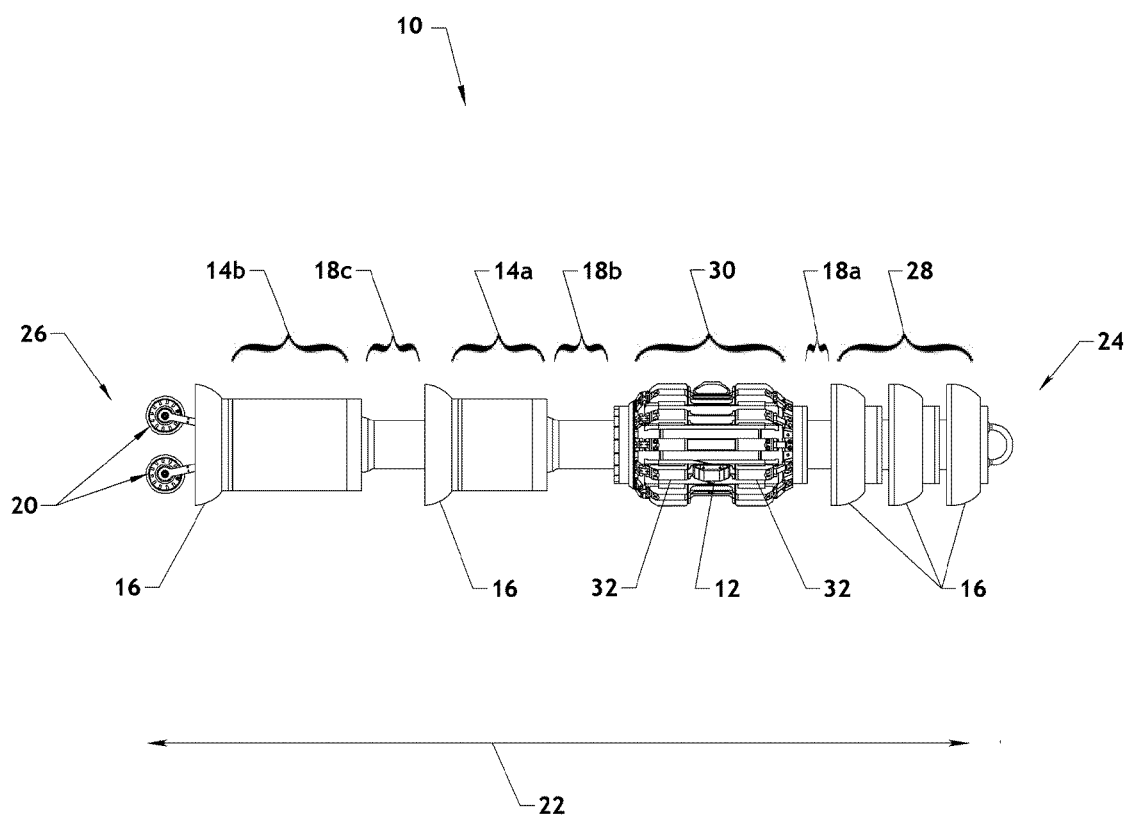
FIG. 1 is an elevation view of one embodiment of an in-line inspection tool in accordance with the present invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention as claimed, but is merely representative of various embodiments of the invention. The illustrated embodiments of the invention will be best understood by reference to the drawings, wherein like parts are designated by like numerals throughout.

Referring to FIG. 1, an in-line inspection tool 10 or vehicle 10 in accordance with the present invention may comprise various components including one or more inspection assemblies 12, canisters 14, driving cups 16, couplers 18, position sensors 20, and the like. Depending on the configuration of the in-line inspection tool 10 and the size of the pipeline to be inspected, the arrangement and number of components (e.g., the number of canisters 14) may vary.

Canisters 14 may house equipment such as one or more processors, memory devices, and batteries. The driving cups 16 may center the tool 10 within the pipeline and enable fluid traveling within a pipeline to engage the tool 10, thereby pushing the tool 10 through the pipeline. In selected embodiments, driving cups 16 may be formed of a somewhat flexible polyurethane or similar material. Couplers 18 may support bending of the tool 10, enabling the tool 10 to accommodate bends in the pipeline. Like the driving cups 16, in selected embodiments the couplers 18 may be formed of somewhat flexible polyurethane or similar material or a mechanical pivoting device.

An in-line inspection tool 10 may extend in a longitudinal direction 22 from a head end 24 to a tail end 26. The various components 12, 14, 16, 18, 20 of an in-line inspection tool 10 may be arranged in series. For example, in the illustrated embodiment, the head end 24 of a tool 10 may comprise a head section 28 comprising one or more driving cups 16. Following the head section 28 may be a primary sensor suite 30. A coupler 18a may extend to connect the head section 28 to the primary sensor suite 30.

In selected embodiments, an in-line inspection tool 10 in accordance with the present invention may include one or more inspection assemblies 12 comprising one or more signal sources, sensors, or combinations thereof positioned so as to travel along the interior of a pipe wall being inspected. Such signal sources and sensors may generate and receive a wide variety of stress waves propagating in any of many directions. While certain embodiments of the present invention may be discussed or illustrated in the context of an in-line inspection tool using EMAT technologies generating magnetostrictive stress waves, is should be understood that concepts in accordance with the present invention are not limited to EMAT technologies and may be applicable to other in-line inspection technologies.

For example, suitable signal sources, sensors, or combinations thereof may include one or more piezoelectric ultrasonic transducers of normal incidence, piezoelectric ultrasonic transducers of oblique incidence, and piezoelectric ultrasonic transducers operating as a phased array. Other suitable signal sources, sensors, or combinations thereof may include one or more pulsed eddy current inspection devices, remote field eddy current devices, and magnetic flux leakage inspection devices.

Following the primary sensor suite 30 may be a first canister 14a. In one embodiment, the first canister 14a may house the hardware providing the processing and memory storage for the in-line inspection tool 10. A coupler 18b may extend to connect the primary sensor suite 30 to the first canister 14a.

The first canister 14a may be followed by another driving cup 16. A coupler 18c may engage a first canister 14a and extend rearward to engage a second canister 14b. In one embodiment, the second canister 14b may house batteries providing the power for the in-line inspection tool 10. In selected embodiments, a driving cup 16 may connect to the second canister 14b. One or more position sensors 20 may then engage the second canister 14b, driving cup 16, or some combination thereof to form the tail end 26 of the in-line inspection tool 10. In one embodiment, the position sensors 20 may comprise one or more odometers 20 positioned to roll along the interior surface of the pipeline and measure the distance traveled by the in-line inspection tool 10.

Figure 2:
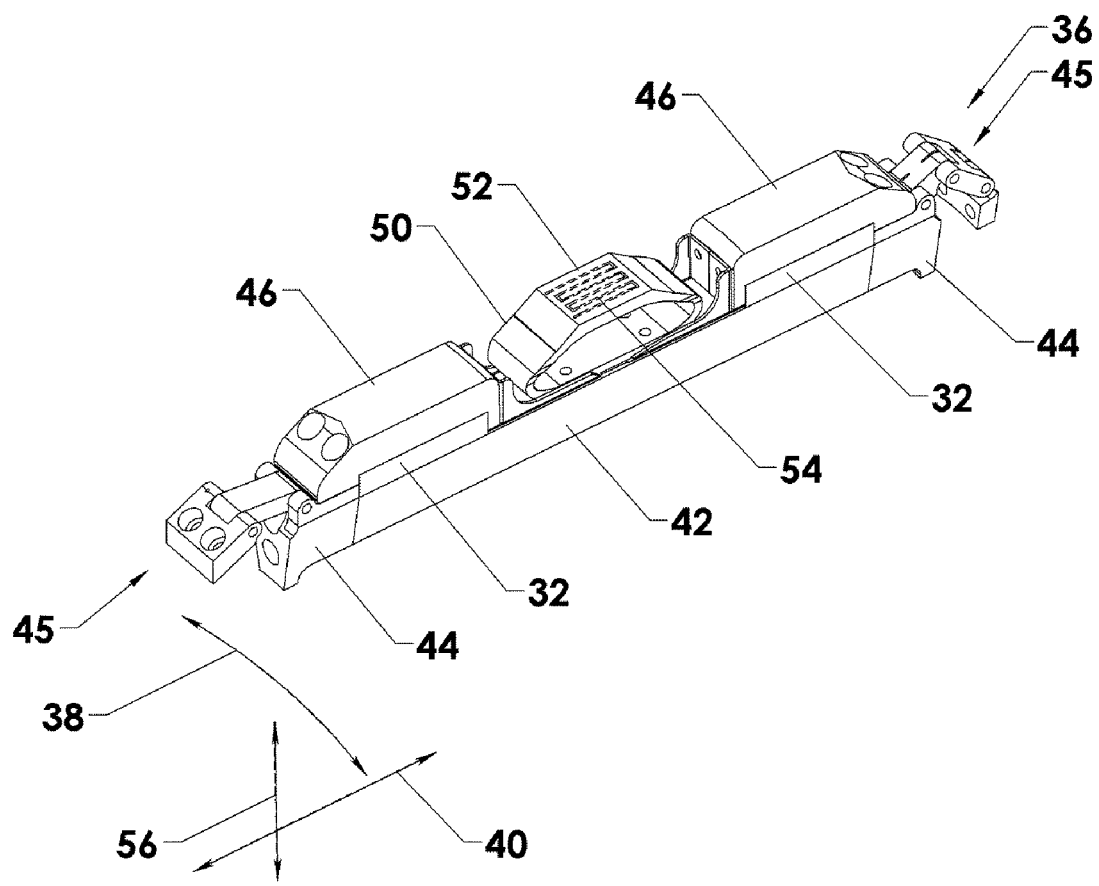
FIG. 2 is a perspective view of one embodiment of an inspection assembly with an EMAT inspection device and linkages positioned with respect to one another as they would be when installed on an in-line inspection tool in accordance with the present invention.

Referring to FIG. 2, in selected embodiments, a primary sensor suite 30 may include inspection assemblies 12 distributed circumferentially (i.e., in a circumferential direction 38) about a central axis 40 of an in-line inspection tool 10. Each inspection assembly 12 may include a back bar 42 for supporting the various components of the inspection assembly 12. A linkage mount 44 may be positioned at each end of a back bar 42. Linkages 45 may engage an inspection assembly 12 via the linkage mounts 44 and extend therefrom to connect the inspection assembly 12 to an interior cylinder (not shown) forming the back bone of the primary sensor suite 30. Suitable linkages 45 are disclosed in U.S. patent application Ser. No. 12/478,137 filed Jun. 4, 2009, which is hereby incorporated by reference. Accordingly, inspection assemblies 12 may partially or fully encircle the interior cylinder.

In embodiments utilizing magnetostrictive EMAT inspection, a magnetic flux field may be introduced into the wall of a pipe by magnets 48. One or more coils 54 may generate and receive or both generate and receive a magnetostrictive stress wave so that anomalies within the wall of the pipe being inspected may be detected.

In selected embodiments utilizing EMAT inspection, a back bar 42 may support one or more magnets 48. In certain embodiments, an inspection assembly 12 may include a magnet mount 46 providing an interface between a back bar 42 and a magnet 48. The magnet mount 46 may protect the magnet 48. The magnet mount 46 may also assist in transferring flux into the wall of the pipe being inspected.

In selected embodiments, a back bar 42 may support two magnets 48, one magnet 48 proximate each end thereof. A sensor mount 50 may secure to the back bar 42 at a location between the two magnets 48. The sensor mount 50 may connect a sensor housing 52 to the back bar 42.

A sensor mount 50 may comprise flexible material. Accordingly, a sensor mount 50 may permit relative motion between a sensor housing 52 and a back bar 42. Constraints such as the magnet mount 46 may be positioned proximate a sensor mount 50 to control or limit certain motion of the sensor mount 50 and sensor housing 52 with respect to the back bar 42. In selected embodiments, a constraint 46 may prevent the sensor housing from contacting or being crushed by the back bar 42. Accordingly, a constraint 46 may provide an additional control over the motion of a sensor housing 52 with respect to a back bar 42.

Inspection assemblies 12 may move with respect to the interior cylinder or main body of an in-line inspection tool 10. For example, inspection assemblies 12 may move in a radial direction 56 with respect to the rest of an in-line inspection tool 10. This freedom of motion may accommodate changes in the pipe being inspected. For example, features such as bends, constrictions, changes in the thickness of the wall of the pipe, circumferential welds, dents, and damaged pipe walls may all affect the interior diameter of a pipeline. Movement of an inspection assembly 12 may permit sensor housings 52 to closely track the interior surface of a pipeline in spite of changes in the interior diameter thereof.

Figure 3:
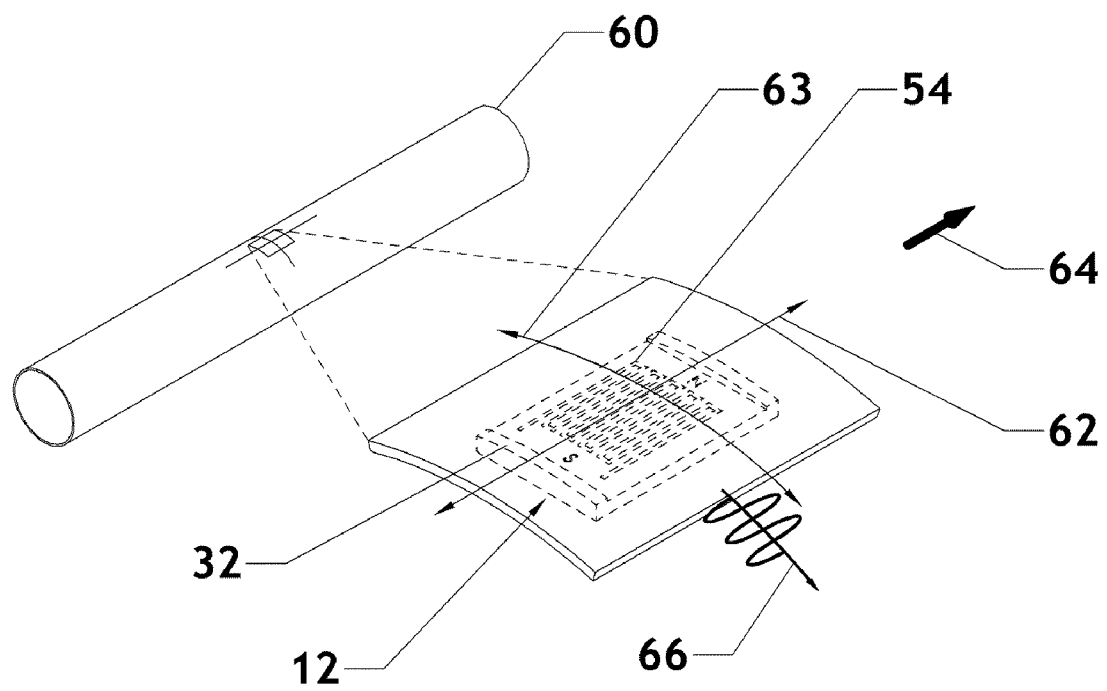
FIG. 3 is a perspective view of a magnetostrictive EMAT inspection device positioned to produce a horizontal shear inspection wave guided circumferentially within the wall of the pipe being inspected in accordance with the present invention.

Referring to FIG. 3, in certain embodiments, an inspection assembly 12 comprising a magnetostrictive EMAT may comprise a transmitting coil 54 (e.g., a meander line coil 54) that may be placed with its long axis parallel to the axis 62 of the pipe 60 being inspected. A magnetic field 64 may be introduced into the pipe wall by the magnets 48 of the inspection assembly 12 such that the field 64 is directed parallel to the long axis of the transmitting coil 54 and along the axis 61 of the pipe 60. When the transmitting coil 54 is activated by an alternating current pulse, a magnetostrictive stress wave 66 (e.g., a horizontal shear wave 66) may be emitted perpendicular to the axis of the coil 54 in the circumferential direction 63 of the pipe 60.

Figure 4:
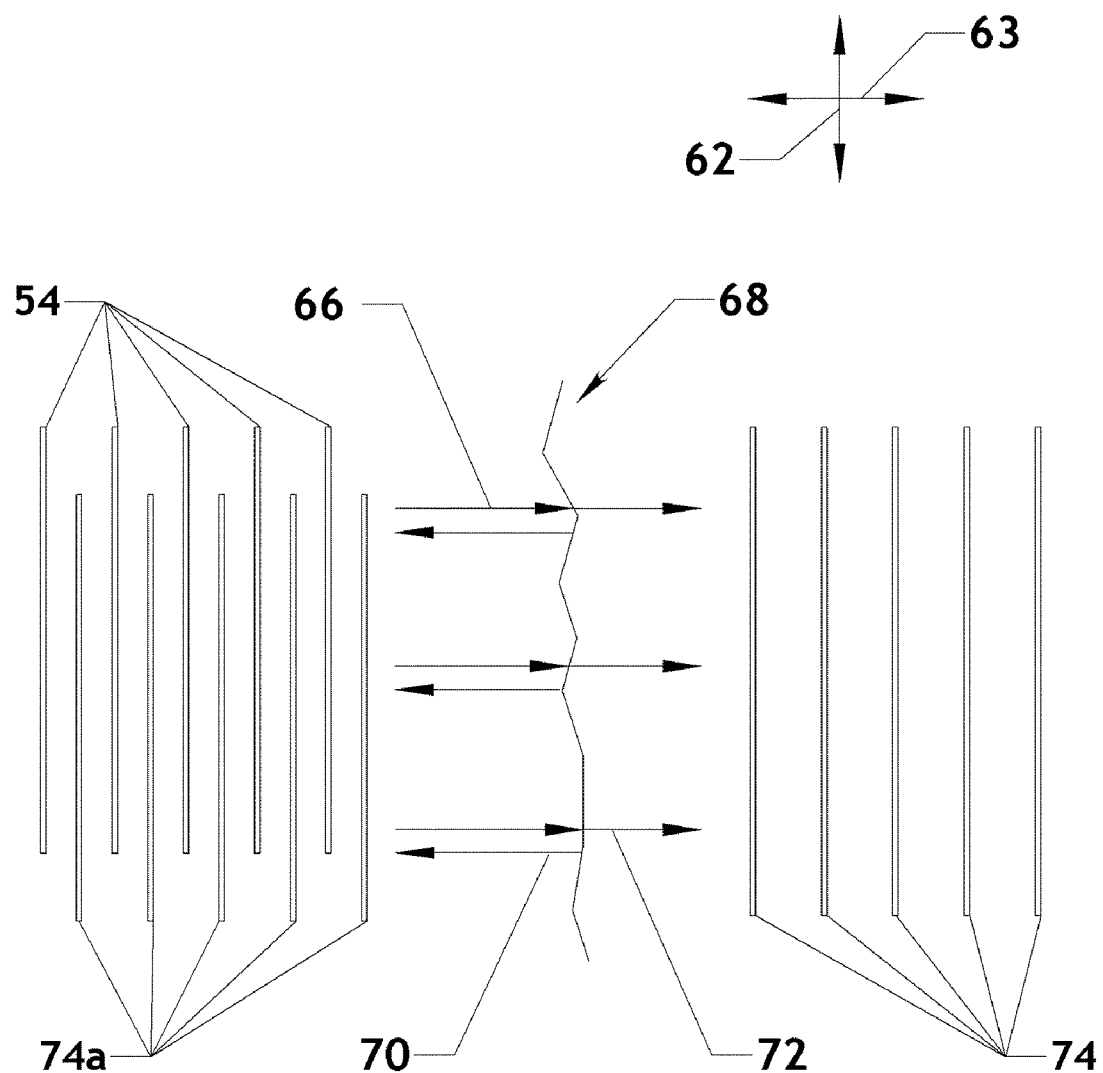
FIG. 4 is a schematic diagram illustrating selected embodiments of elements of coils of an EMAT in-line inspection tool showing their positions relative to one another and to signals generated and/or received thereby in accordance with the present invention.

Referring to FIG. 4, in selected embodiments, once produced the horizontal shear wave 66 may be guided by the surfaces of the pipe wall to travel around the circumference of the pipe 60. In so doing, the wave 66 may encounter an obstruction such as a defect 68 in the pipe wall. A defect 68 may produce a reflected pulse 70 that can be received at or near the location of the transmitting coil 54 in a pulse-echo mode. A defect 68 may also alter the portion 72 of the wave 66 that passes the defect 68.

The altered wave 72 may be received by a receiving coil 74 located past the defect 68 in a pitch-catch mode. This receiving coil 74 may be located anywhere up to 360° around the pipe 60 in the circumferential direction 63 where it would overlay the transmitting coil 54. At 360° the receiving coil 74 may be the transmitting coil 54 itself in a non-transmitting mode. The receiving coil 74 may be placed even slightly more than 360° around the circumference of the pipe 60. Accordingly, the entire circumference of the pipe 60 may be inspected by one or more such devices 54, 74.

Embodiments in accordance with the present invention may include any suitable combination of transmitter and receiver including, without limitation, a transmitting coil 54 used as both a transmitter and receiver in a pulse-echo mode; a transmitting coil 54 with a separate, comparable receiving coil 74a placed within the magnetic bias field 64 or in a similar bias field slightly ahead of the transmitting coil 54 in a pulse-echo mode; a transmitting coil 54 with a comparable receiving coil 74 in a comparable magnetic bias field placed beyond the location of potential axially oriented defects 68 in a pitch-catch mode; a transmitting coil 54 used as a transmitter and receiver in a pitch-catch mode for guided waves traveling 360° completely around the circumference of the pipe; or a transmitting coil 54 with a separate comparable receiving coil 74a placed within the magnetic bias field 64 or in a similar bias field slightly removed from the transmitting coil 54 in a pitch-catch mode for guided waves 66 traveling just under or just over 360° around the circumference of the pipe 66.

Full coverage of the pipe cross section may be enhanced by using one inspection assembly 12 as described or by two or more of the described inspection assemblies 12 offset from one another along the pipe axis 62 with their transmitting coils 54 offset from one another circumferentially as well. In one embodiment, an in-line inspection tool 10 in accordance with the present invention may include three inspection assemblies 12 operating in accordance with the foregoing. The three inspection assemblies 12 positioned equidistant from one another in the circumferential direction 38 around the tool 10.

In embodiments where the direction of the magnetic field 64, the direction of the axis of the transmitting coil 54, or the configuration of the receiving coil 54 may be different from the embodiment illustrated, other stress waves may also be emitted. To isolate the waves used for inspection, waves extraneous to the inspection may be removed by frequency filtering, time gating, digital signal processing or other techniques consistent with the nature of the initiating pulse.

Figure 5:
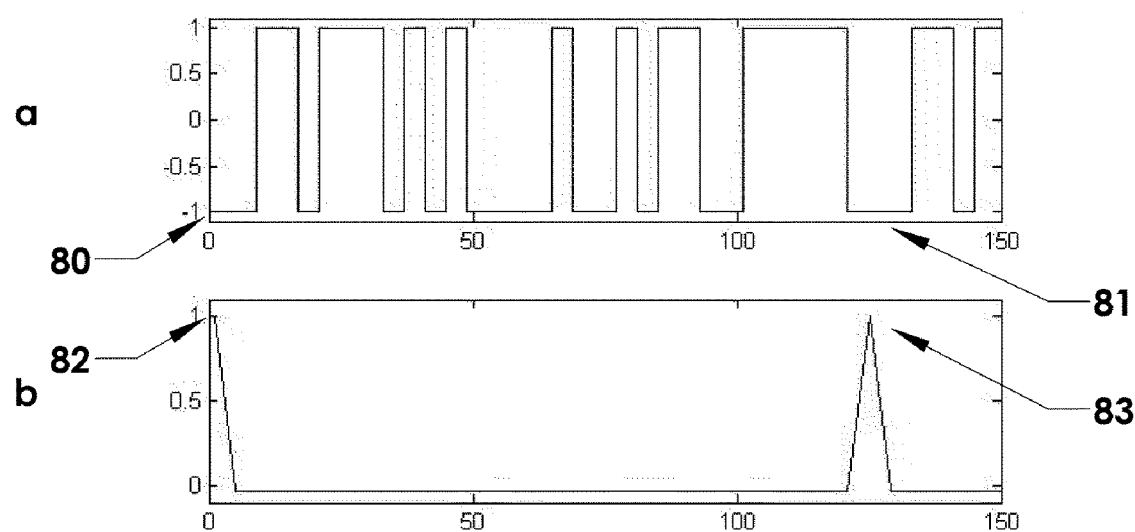
FIG. 5 is an illustration showing one embodiment of a pseudorandom binary sequence (PRBS) and the Delta function autocorrelation thereof.

Referring to FIG. 5, the pipeline environment is noisy. Accordingly, low level signals propagating through a pipeline environment may be partially or entirely obscured by ambient background noise from pipeline activity, movement an-line tool through the pipeline, etc. In the past, to have operated in the noisy pipeline environment, an in-line inspection tool using EMAT would have required large, high power equipment to produce a signal strong enough to be visible above ambient pipeline background. However, such equipment is incompatible with the confined spaces and limited power of in-line inspection tools. As a result, few EMAT in-line inspection tools exist in the market today.

To overcome the noisy pipeline environment, selected embodiments in accordance with the present invention combine low level inspection signals with a pseudorandom binary sequence (PRBS) to improve the tool's 10 ability to detection the inspection signals. That is, the pseudorandom binary sequence may be used to separate the inspection signal from ambient background signal or ambient noise. By so doing, technologies such as EMAT become practical because low level signals may be generated by smaller transducers that consume much less power.

A PRBS may comprise a sequence of analytically manageable binary signals formulated to represent a period of random noise that typically would not be analytically manageable. Correlation is a mathematically defined term that essentially measures how well a function will match another function. If the functions are identical, correlation will have a value of 1, which means that a period of the signal will exactly match the same period of the identical function when the two periods overlay one another. A PRBS is formulated as a periodic function with continual repetition of the period.

Autocorrelation is the correlation of a function with itself. Cross correlation is the correlation of one function with another function. Each of these terms is also mathematically defined. A true random number sequence will auto correlate perfectly with itself to produce a delta function, or a function with a value of one where the function overlays itself once each period and a value of zero everywhere else.

A basic PRBS is illustrated in FIG. 5a. The sequence consists of binary values of 1 or −1 and is periodic from a beginning point 80 to an ending point 81. As shown in FIG. 5b, autocorrelation of the basic PRBA of FIG. 5a produces an approximation of a delta function. Peaks 82 and 83 in the auto correction function appear at the points where the basic PRBA auto correlates with itself, separated by one period. Periods may be represented in time.

Figure 6:
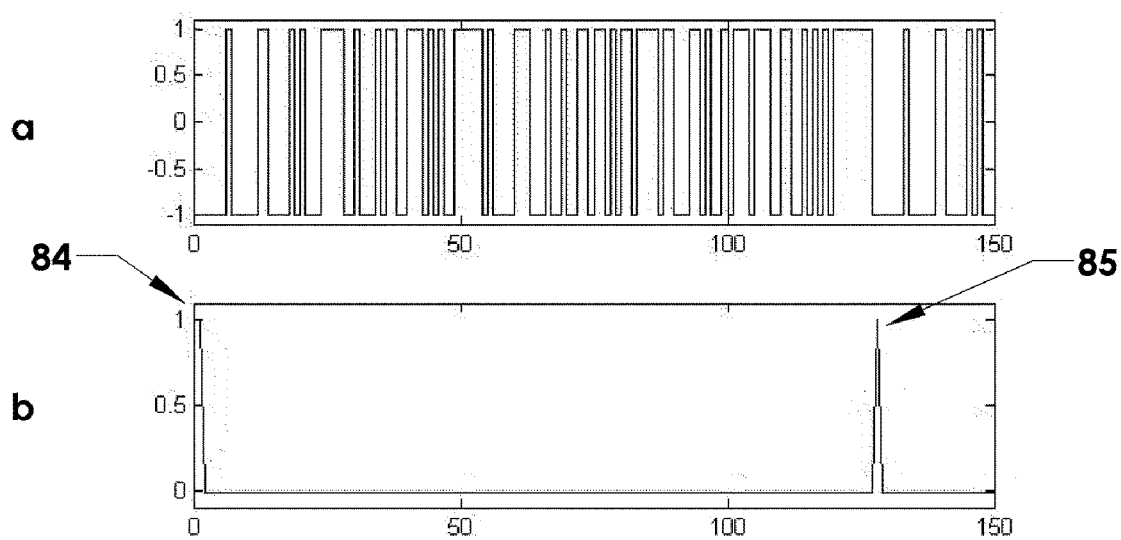
FIG. 6 an illustration showing another embodiment of a pseudorandom binary sequence and the Delta function autocorrelation thereof.

Referring to FIG. 6, different PRBSs can operate at different frequencies (e.g., average frequencies). For example, the PRBS of FIG. 6a has a significantly higher frequency than does the basic PRBS of FIG. 5a. FIG. 6b illustrates the autocorrelation function corresponding to the PRBS of FIG. 6a. This autocorrelation function demonstrates that increased signal frequency produces an improved approximation of the delta function with sharper nodes as shown by the resulting peaks 84 and 85.

Figure 7:
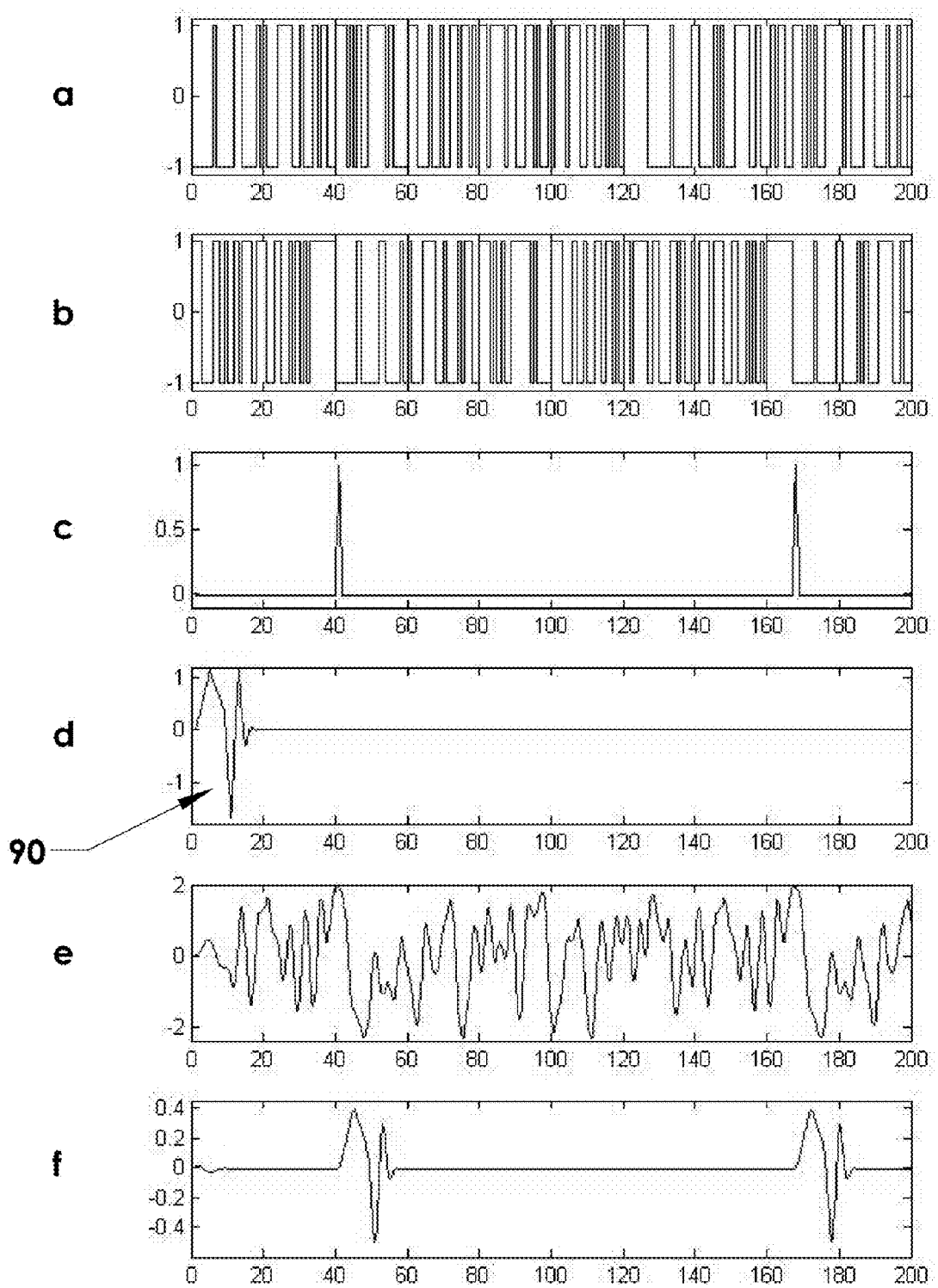
FIG. 7 is an illustration showing from top to bottom a first PRBS, a time delayed version of the first PRBS, an autocorrelation of the first PRBS and the time delayed version, a typical incident pulse as may be generated by an in-line inspection tool in accordance with the present invention, a convolution of the first PRBS and the typical incident pulse delayed by time, and a cross correlation of the time delayed convolution and the original version of the PRBS.

Referring to FIG. 7, a working model of a PRBS is illustrated. A first PRBS is shown in FIG. 7a. A time delayed version of the first PRBS is shown in FIG. 7b. The autocorrelation function of the first PRBS with the delayed version of itself is shown in FIG. 7c. An inspection pulse 90 (e.g., wave 66) that may be generated by an inspection assembly 12 (e.g., a magnetostrictive EMAT 12) is shown in FIG. 7d. This pulse 90 may have a low power and would be difficult to identify in a noisy background. To improve its detectability, the pulse 90 is combined or convoluted with the PRBS (i.e., the signal of FIG. 7a). The resulting convolution as delayed by travel time is shown in FIG. 7e. When the convoluted signal of FIG. 7e is cross correlated with the reference PRBS of FIG. 7a, the result is the correlation function of FIG. 7f, which reveals the pulse 90 with a time delay equal to the delay of the delayed version of the first PRBS.

In operation, the convoluted signal (e.g., the signal of FIG. 7e) may be transmitted by an inspection assembly 12 (e.g., EMAT 12). As the convoluted signal travels through the wall of the pipe 60 being inspected, it may be affected by defects or other anomalies in the wall. On reception by a receiver, the convoluted signal may be cross correlated with the reference PRBS. The resulting cross correlation function 7f may then reveal the inspection signal or pulse 90.

In operation, the time delay before an inspection wave or pulse 90 may be equal to the travel time of the signal 90 from transmission to reception. Knowing the speed of travel of the stress wave 90 in the pipe wall material allows calculation of the distance between a transmitter/receiver and a defect 68.

Figure 8:
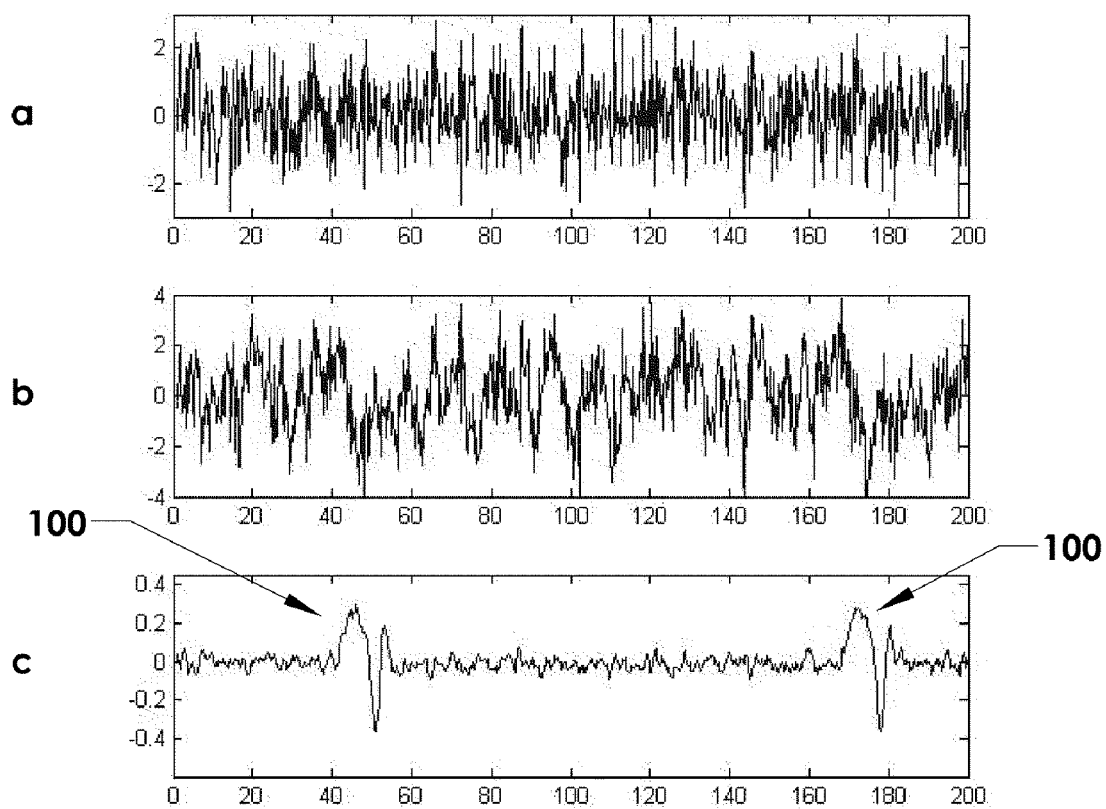
FIG. 8 is an illustration showing from top to bottom an inspection pulse obscured in typical background noise as may be found in a pipeline environment, a convolution of an inspection pulse and a PRBS together with the background noise, and a cross correlation of the convoluted pulse in the background noise and the original PRBS.

In a noisy pipeline environment, the pulse 90 of FIG. 7d would be totally obscured. However, using the apparatus and methods in accordance with the present invention, an inspection pulse 90 may be identified despite the background noise. For example, FIG. 8a shows the pulse 90 of FIG. 7d in background noise from the pipeline environment and the pulse is entirely obscured. As used in the invention, FIG. 8b shows the transmitted signal of FIG. 7e (which is a convolution of the pulse and the PRBS delayed by travel time) in the noisy background. Thus, the signal shown in FIG. 8b may be comparable to the signal received by a receiving coil 74 in accordance with the present invention.

When the signal of FIG. 8b is cross correlated with the original PRBS of FIG. 7a the function of FIG. 8c is obtained. The function clearly shows the inspection pulse 100 somewhat modified by the effects of travel and delayed by travel time. It clearly evidences the shape of the original pulse 90. The random noise in the environment is uncorrelated and drops out. Accordingly, anomalies 68 in the pipe wall may be thus identified and located. Characteristics of the anomalies 68 may be determined by alteration of the pulse shape as it is reflected by or partially passes by the anomaly 68.

Figure 9:
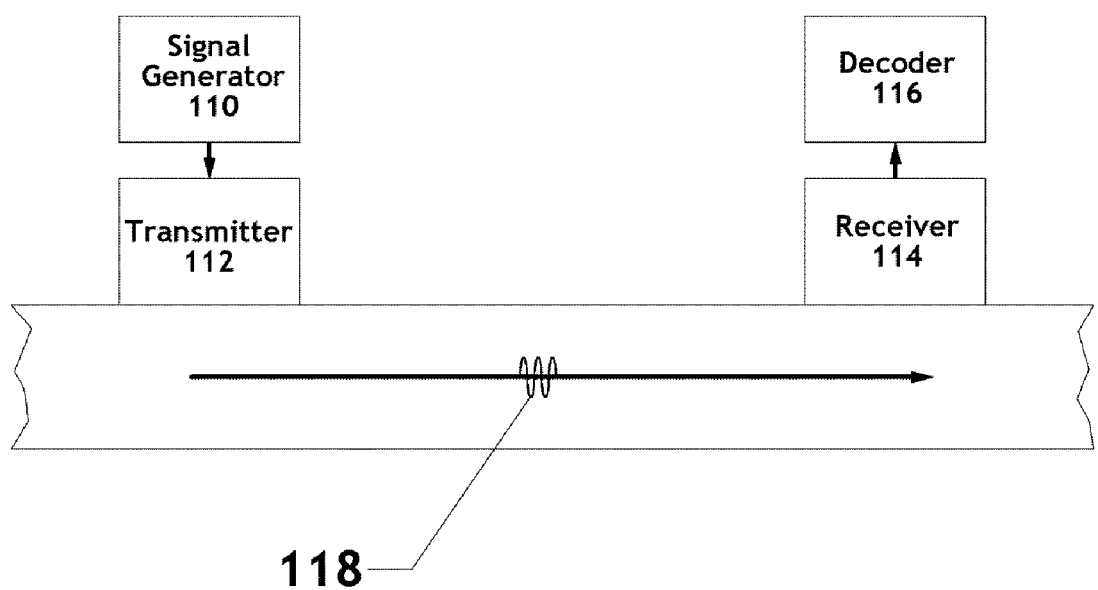
FIG. 9 is a schematic block diagram of one embodiment of a PRBS-based system for generating and receiving an inspection pulse in a pipe wall in accordance with the present invention.

Referring to FIG. 9, one embodiment of an in-line inspection tool 10 in accordance with the present invention may include a signal generator 110, transmitter 112, receiver 114, decoder 116, and other components as desired or necessary. A signal generator 110 may be formed using software, hardware, or some combination thereof. In operation, a signal generator 110 may generate a PRBS and convolute the PRBS with an input pulse to pass a coded pulse to a transmitter 112 (e.g., EMAT). In certain embodiments, the signal driving the transmitter 112 thus may be the convolution output from the signal generator 110.

The transmitter 112 may induce a signal 118 into the pipe wall. In embodiments where the transmitter 112 comprises an EMAT, the inherent characteristics of EMAT technology may result in a relatively low strength signal 118 in the pipe wall. As the convoluted signal 118 travels through the pipe wall, it may encounter defects in the pipeline. These defects may produce reflections received by a receiver 114. A decoder 116 may then correlate the signal received by the receiver 114 with a reference pseudorandom signal. In this manner, the weak inspection signal may be identified despite low signal strength and noise in the environment, even when the signal-to-noise ratio is relatively low and may even be less than one.

In-line inspection tools 10 based on technologies other than EMAT are hindered by the same noise effects. While the present invention may be described herein in the context of a magnetostrictive EMAT in-line inspection tool 10, the present invention may be used in conjunction with other sensing technologies. For example, the present invention may be applied to in-line inspection tools utilizing ultrasonic inspection (UT), eddy current inspection, Lohrentz Force electromagnetic acoustic transducer (EMAT) inspection, and the like.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An in-line inspection tool for inspecting the wall of a pipeline while traveling through the pipeline, the in-line inspection tool comprising:
    a transmitter;
    a signal generator generating a pseudorandom signal, generating an inspection signal, and driving the transmitter with a convolution of the pseudorandom signal and the inspection signal;
    the transmitter transmitting, in the form of a transmitted stress wave traveling primarily circumferentially, the convolution to the wall of the pipeline; and
    one or more receivers detecting in the wall of the pipeline a received stress wave after the received stress wave has traveled circumferentially at least about 120 degrees within the wall of the pipeline, the one or more receivers outputting a received signal comprising at least one of the convolution and a reflection of the convolution.

2. The in-line inspection tool of claim 1, wherein the transmitter and receiver each comprise one or more magnetostrictive electromagnetic acoustic transducers.

3. The in-line inspection tool of claim 1, wherein the transmitter and receiver each comprise one or more Lohrentz force electromagnetic acoustic transducers.

4. The in-line inspection tool of claim 1, wherein the transmitter and receiver each comprise an electromagnetic acoustic transducer.

5. The in-line inspection tool of claim 1, wherein the transmitter and receiver each comprise one or more piezoelectric ultrasonic transducers.

6. The in-line inspection tool of claim 5, wherein the one or more piezoelectric ultrasonic transducers operate at one of normal incidence and oblique incidence.

7. The in-line inspection tool of claim 5, wherein the one or more piezoelectric ultrasonic transducers operate as a phased array.

8. The in-line inspection tool of claim 1, further comprising a decoder identifying the inspection signal within the received signal by cross correlating the received signal and the pseudorandom signal.

9. A method comprising:
    selecting an in-line inspection tool comprising a transmitter, signal generator, and one or more receivers;
    inserting the in-line inspection tool within a pipeline having a wall;
    generating, by the signal generator, a pseudorandom signal;
    generating, by the signal generator, an inspection signal;
    driving, by the signal generator, the transmitter with a convolution of the pseudorandom signal and the inspection signal;
    transmitting, by the transmitter in response to the driving, the convolution to the wall of the pipeline in the form of a transmitted stress wave traveling primarily circumferentially within the wall;
    receiving, by the one or more receivers, a received stress wave from the wall of the pipeline after the received stress wave has traveled at least about 360 degrees circumferentially around the pipeline;
    generating, by the one or more receivers in response to the receiving, a received signal comprising at least one of the convolution and a reflection of the convolution; and
    identifying the inspection signal within the received signal by cross correlating the received signal and the pseudorandom signal.

10. The method of claim 9, wherein the transmitter and one or more receivers each comprise one or more magnetostrictive electromagnetic acoustic transducers.

11. The method of claim 9, wherein the transmitter and one or more receivers each comprise one or more Lohrentz force electromagnetic acoustic transducers.

12. The method of claim 9, wherein:
    the transmitter and receiver each comprise one or more piezoelectric ultrasonic transducers; and
    the one or more piezoelectric ultrasonic transducers operate at one of normal incidence and oblique incidence.

13. The method of claim 9, wherein:
    the transmitter and receiver each comprise one or more piezoelectric ultrasonic transducers; and
    the one or more piezoelectric ultrasonic transducers operate as a phased array.

14. A method of inspecting a pipeline, the method comprising:
    selecting a pipeline having a wall;
    selecting an in-line inspection tool comprising a transmitter and a receiver;
    traveling, by the in-line inspection tool, within the pipeline;
    transmitting, by the transmitter during the traveling, a convolution of a pseudorandom signal and a inspection signal to the wall of the pipeline in the form of a transmitted stress wave traveling primarily circumferentially within the wall;
    receiving, by the receiver, a received stress wave from the wall of the pipeline after the received stress wave has traveled at least about 120 degrees circumferentially around the pipeline;
    generating, by the receiver in response to the receiving, a received signal comprising at least one of the convolution and a reflection of the convolution; and
    identifying the inspection signal within the received signal by cross correlating the received signal and the pseudorandom signal.

15. The method of claim 14, wherein the transmitter and receiver each comprise one or more magnetostrictive electromagnetic acoustic transducers.

16. The method of claim 14, wherein the transmitter and receiver each comprise one or more Lohrentz force electromagnetic acoustic transducers.

17. The method of claim 14, wherein the transmitter and receiver each comprise an electromagnetic acoustic transducer.

18. The method of claim 14, wherein the transmitter and receiver each comprise one or more piezoelectric ultrasonic transducers.

19. The method of claim 18, wherein the one or more piezoelectric ultrasonic transducers operate at one of normal incidence and oblique incidence.

20. The method of claim 18, wherein the one or more piezoelectric ultrasonic transducers operate as a phased array.

* * * * *